US006892491B2

(12) United States Patent
Hedman

(10) Patent No.: US 6,892,491 B2
(45) Date of Patent: May 17, 2005

(54) SYSTEM AND METHOD FOR REMOVING HARMFUL BIOLOGICAL AND ORGANIC SUBSTANCES FROM AN ENCLOSURE

(76) Inventor: David E. Hedman, 7750 Sulphur Mountain Rd., Ojai, CA (US) 93023

( * ) Notice: Subject to any disclaimer, the term of this patent is extended or adjusted under 35 U.S.C. 154(b) by 0 days.

(21) Appl. No.: 10/218,150

(22) Filed: Aug. 12, 2002

(65) Prior Publication Data

US 2002/0189154 A1 Dec. 19, 2002

Related U.S. Application Data

(63) Continuation-in-part of application No. 09/768,680, filed on Jan. 24, 2001, now abandoned, which is a continuation-in-part of application No. 09/321,915, filed on May 28, 1999, now Pat. No. 6,327,812.

(51) Int. Cl.[7] .............................................. A01M 1/20
(52) U.S. Cl. ........................... 43/132.1; 43/124; 43/139
(58) Field of Search ................................ 43/124, 132.1, 43/139

(56) References Cited

U.S. PATENT DOCUMENTS

| | | | | |
|---|---|---|---|---|
| 1,885,854 A | * | 11/1932 | Montellano | 43/139 |
| 3,750,327 A | * | 8/1973 | Thybault | 43/139 |
| 4,817,329 A | * | 4/1989 | Forbes | 43/124 |
| 4,953,320 A | * | 9/1990 | Nelson | 43/132.1 |
| 4,958,456 A | * | 9/1990 | Chaudoin | 43/124 |
| 4,989,363 A | * | 2/1991 | Doernemann | 43/124 |
| 5,058,313 A | * | 10/1991 | Tallon | 43/124 |
| 5,349,778 A | * | 9/1994 | Chu | 43/132.1 |
| 5,442,876 A | * | 8/1995 | Pedersen | 43/124 |
| 5,768,907 A | * | 6/1998 | Lee | 43/132.1 |
| 5,806,238 A | * | 9/1998 | Brenner | 43/139 |
| 6,141,901 A | * | 11/2000 | Johnson | 43/124 |
| 6,327,812 B1 | * | 12/2001 | Hedman | 43/124 |

* cited by examiner

*Primary Examiner*—Kurt Rowan
(74) *Attorney, Agent, or Firm*—Kelly Lowry & Kelley, LLP

(57) ABSTRACT

A system and method for removing harmful biological and organic substances from an enclosure, vehicle or container includes protecting heat-sensitive articles within the enclosure. A plurality of temperature probes are positioned at predetermined locations within the enclosure. The air within the structure is heated to a predetermined temperature up to 400° F. to kill organisms and cause harmful substances in the enclosure to migrate into the ambient air. A negative pressure is created in the enclosure and the heated air carrying the harmful substances passed through a filter and is then vented from the enclosure and passed through a filter to remove the harmful substances from the heated air. The system effectively kills, molds, viruses and bacteria and reduces the levels of allergens and volatile organic compounds in the enclosure.

18 Claims, 2 Drawing Sheets

SYSTEM AND METHOD FOR REMOVING HARMFUL BIOLOGICAL AND ORGANIC SUBSTANCES FROM AN ENCLOSURE

RELATED APPLICATION

This application is a continuation-in-part of U.S. application Ser. No. 09/768,680, filed Jan. 24, 2001 now abandoned, which is a continuation-in-part of U.S. application Ser. No. 09/321,915, filed May 28, 1999 now U.S. Pat. No. 6,327,812.

BACKGROUND OF THE INVENTION

The present invention relates to methods of sanitizing buildings and other enclosed or enclosable spaces. More particularly, the present invention relates to a system and method for killing and removing bacteria, viruses, fungi, toxic molds, and volatile organic compounds.

Techniques of varying effectiveness have been developed using heated air or very cold air to kill termites and other organisms. Typical of these are the methods disclosed by Charles Forbes in U.S. Pat. No. 4,817,329, and Hedman et al. in U.S. Pat. No. 6,327,812 in which wood destroying insects, e.g., termites, are killed by applying a heated gas, such as heated air, to wooden surfaces or the like until the building surfaces are heated to a temperature, typically about 120° F. to 135° F. Temperatures for killing other insects are said to be surprisingly close to this range. This method has been found to be very effective for killing termites.

However, the methods disclosed in the Forbes and Hedman et al. patents are quite complex in the preparation of the building. An enclosing tent structure must be formed around the structure to be decontaminated. Tenting the building with heavy tarpaulins requires workers to walk and arrange the tarpaulins on the roof, often damaging the roof system. Also, this method, using the described temperatures, is not effective for other organisms, such as fungi, and toxic molds such as, but not limited to, *aspergillus oryzae, aspergillus terreus, aspergills versicolor, cladosporium hergbarum, stachybotrys chartarum, penicillium aurantiogriseum, pencillium chrsogenum, pencillium gladrum* and *fusarium oxysporum*. Further, many such fungi, molds and the like are a serious health hazard even when dead. Many people are allergic to the dust-like remains, i.e., allergens, of these organisms that can also cause serious health problems. This is a particular problem to persons suffering from asthma, bronchitis, pneumoconious and other respiratory ailments, and is a common contributing factor to sick building syndrome (SBS).

It is also well-known that the heated air causes certain molds, fungi, etc. to sporulate, thus releasing spores into the structure and thus dispersing the harmful biological agents and possibly contaminating the structure to a greater degree than originally presented. The use of positive pressure within the structure, as described in Forbes and Hedman et al., further increase the likelihood that the biological contaminants will be dispersed throughout the structure Forbes and Hedman et al. also disclose that the heated air can be vented from open windows and the like. However, when treating a contaminated building having harmful viruses, toxic molds, etc., it is not desirable to release such contagions into the air.

Volatile organic compounds (VOCs) have also been implicated as a possible cause of SBS. VOCs can originate from a variety of sources. Commercial examples include by-products of printing shop operations, office machine repairs, blueprint production, photographic processing and food service operations. In residences, such VOCs can include hobbyist products, cosmetics, perfumes, personal hygiene products, aerosol sprays, tobacco smoking, pet urine and even small emissions from the bodies of the occupants. Off gassing of VOCs is often a common by-product of various building/construction materials, for example paints, adhesives, plastics, carpeting, etc.

Such VOCs are implicated with SBS for mostly two reasons. First, the health effects from exposure to VOCs are consistent with SBS, ranging from irritant effects such, as unpleasant odors and mucous membrane irritation, through general systemic effects such as fatigue, nausea, and difficulty concentrating. In addition, they may be of importance because some of them have been shown to have carcinogenic or adverse reproductive effects. Second, indoor concentrations of VOCs, particularly in new buildings, are often greatly elevated with respect to outdoor VOC concentrations. In fact, indoor VOC concentrations have typically been found to be two to ten times higher then outdoor concentrations, and indoor concentrations as much as 100 times higher than outdoor concentrations have been reported in new buildings.

Accordingly, there is a need for a system and method for killing and removing biological organisms and reducing odors and volatile organic compounds in enclosures such as commercial and residential buildings, boats, vehicles and product containers. Such a method should be non-toxic and performed in a relatively short amount of time. Such a method should also effectively kill and remove a large proportion of the dead organisms and substantially reduce volatile organic compounds. The present invention fulfills these needs and provides other related advantages.

SUMMARY OF THE INVENTION

The present invention resides in a system which removes harmful organic substances from an enclosure, such as a building, vehicle, container or other enclosed structure. The structure is typically prepared by positioning a plurality of temperature probes at predetermined locations within the structure. A manometer is positioned to measure the pressure, as will be more fully described herein. Heat-sensitive articles within the structure are protected. This can be done by covering the articles with an insulated mat. Also, fans can be positioned adjacent to the heat sensitive articles for directing the flow of heated air away from the articles during the decontamination process. The contaminated area of the structure may also be physically cleaned in preparation of decontamination. This can be done by wiping, scraping, vacuuming, etc. the mold or other harmful organisms which are accessible and can be easily cleaned and removed.

A negative pressure is then created within the structure. The ambient air within the structure is then heated to a predetermined temperature of between 110° F. and 400° F., typically by directing and distributing heated air into the enclosed structure. This causes the harmful substances in the structure to be destroyed or migrate into the ambient air. Preferably, the air within the structure is aggressively moved using blowers, fans, or the like to aerosolize the biological and organic substances to facilitate the removal. The temperature of the structure is monitored until the predetermined temperature is achieved. The pressure levels within the structure are also monitored to verify adequate negative pressure.

The heated air carrying the harmful substances are then removed from the structure through a filter. The filter preferably comprises a high efficiency particulate arrestance filter. In a particularly preferred embodiment, after a predetermined time period of directing heated air within the structure, the non-heated ambient air is directed into the structure, while continuing to remove the air through the filter. In certain instances, the contaminated portion of the structure is then physically cleaned after these steps have been performed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
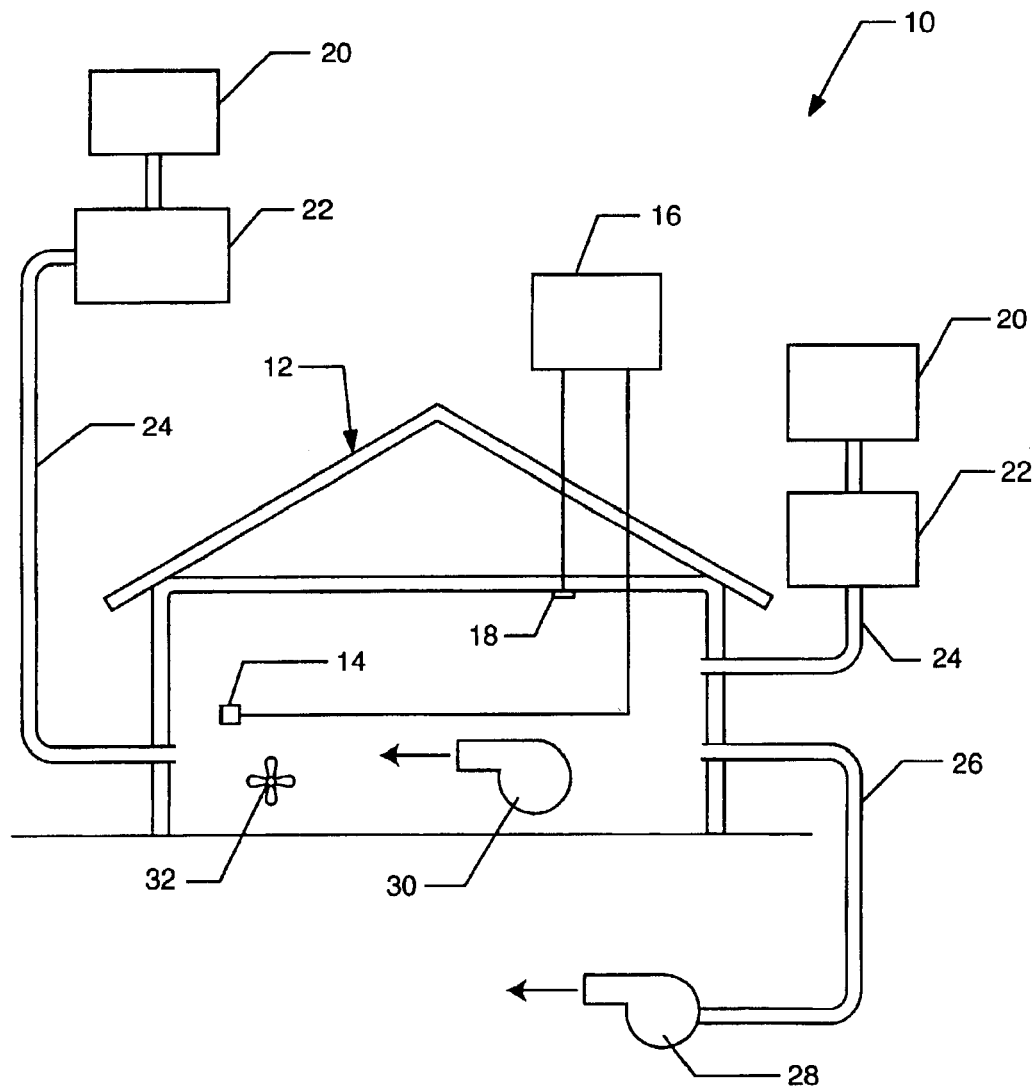
FIG. 1 is a schematic diagram showing components of the system of the present invention.

Referring to FIG. 1, there is seen a schematic diagram showing the components of the system of the present invention, referred to generally by the reference number 10, in use treating an enclosed structure 12. The enclosed structure 12 is typically a commercial or residential building, but may be a boat, vehicle, product container or dedicated decontamination chamber.

A plurality of temperature sensors 14 are positioned at predetermined locations to monitor the temperature of the structure 12. Typically, these sensors 14 have thin, elongated tips that can be adhered to or pushed into materials to be heated or into suitably sized holes drilled into such materials so as to measure the surface and/or internal temperature. The sensors 14 may be wired to a console 16 which displays and records the temperature at each sensor 16 in real time. Alternatively, the sensors 14 may be wireless and transmit a signal to the console 16. Typical sensors 14, as for way of example and not by way of limiting, include thermal couples, thermistors, or the like connected to a computer and/or a strip chart recorder console 16.

A pressure measuring device, such as a manometer 18, is positioned within the structure 12 so as to measure the internal pressure of the structure 12 during operation of the invention. As will be more fully described herein, it is imperative that a negative pressure be established and maintained throughout the operation of the invention in order to remove the harmful biological and organic contaminants and prevent their dispersal throughout the structure 12. The manometer 18 can be linked to the console 16 to provide the pressure information from without the structure 12.

One or more heaters 20 heat air to a predetermined temperature. The air is heated to at least a temperature lethal to the organisms to be destroyed. For a more complete disinfection, the air temperature is preferably raised to at least about 155° F., with optimum results generally be achieved with temperatures in the range of about 110° F. to 400° F., or higher. A biocide, having desirable characteristics enhanced by heat, may be introduced with the heated air.

Any suitable heater 20 may be used. A gas burning heating device 20, such as a conventional propane heater, is preferred as being particularly efficient in heating air. Any other heating arrangement, such as electrical devices, solar heaters, and light emitting devices, may be used if desired.

Heated air (and biocide, if used) from the one or more heaters 20 is directed through blower 22 (which may, if desired, be a component of the heater 20) which injects the hot air into the enclosed structure 12 through at least one inlet duct 24. Generally, a plurality of inlet ducts 24 will be used to achieve the optimum distribution of hot air throughout the enclosed structure 12. The inlet ducts 24 preferably include variable flow dampers and may be moved while the system is in operation to achieve uniform temperatures in all areas of the structure being treated, as sensed by sensors 14 and observed at console 16. Moisture may be introduced with the heated air.

At least one outlet duct 26 is provided to allow the air to be removed from the structure 12. A blower or vacuum 28 is connected to the outlet duct 26 in order to remove air from the interior of the structure 12 and create negative pressure within the structure 12. Typically, this negative pressure is created before the heated air is introduced into the structure 12. The removed air is filtered, typically utilizing a high particulate arrestance filter, ULPA filter, or the like coupled with the vacuum/blower 28. The filter or air scrubber removes the remains of the organisms and VOCs from the air to prevent them from reaching the environment. Other filters such as charcoal filters or UV filters may be employed as well.

Preferably, additional blowers 30 or fans are positioned within the structure 12 to aggressively move the air within the structure to further enhance the removal of harmful biological and organic substances by aerosolizing the biological and organic substances and aid in heat distribution. Additionally, fans 32 may be positioned strategically within the structure 12 to selectively move the air away from predetermined heat-sensitive articles or areas of the structure in which such an elevated temperature is not desired. Typically, however, such heat-sensitive articles are removed from the structure or covered with insulation mats or the like.

Figure 2:
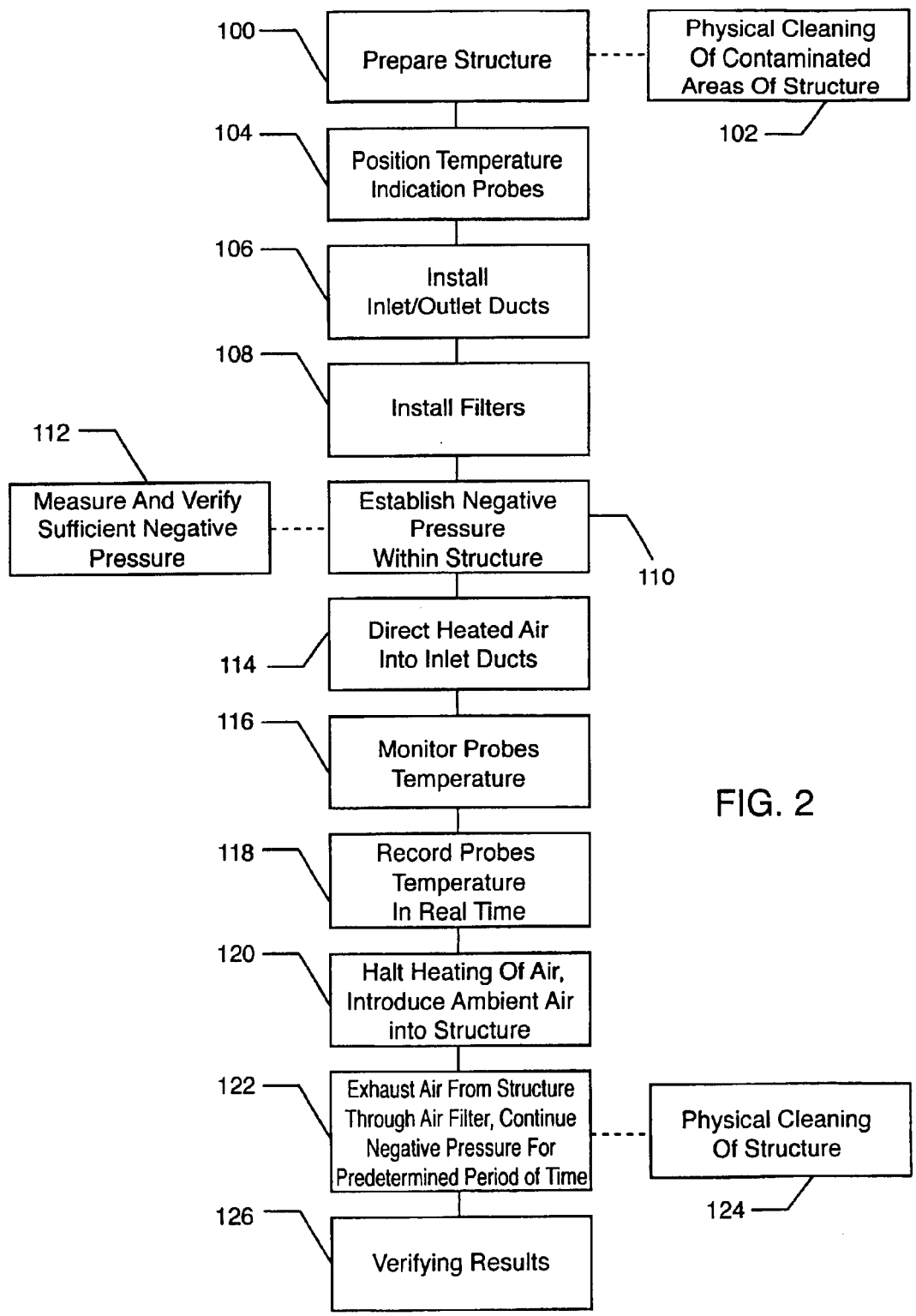
FIG. 2 is a flow diagram of the method of the present invention.

With reference to FIG. 2, in the operation of the system of the invention, the first step is to prepare the structure, as indicated in block (100). This basically involves removing all heat-sensitive items from the enclosure or, in some cases, covering heat sensitive items, such as electronic devices and plastic items, with thermal insulation material. All material that has a flash/melt point or below the maximum temperature to be used (such as candles, lipstick, etc.) must be removed.

Typically, the preparation in the structure also includes physical cleaning of contaminated areas of the structure (102) while the area is under a negative pressure. This can include vacuuming, wiping, scraping, etc. of various surfaces which have been contaminated with harmful biological contaminants, such as mold, fungi, etc. In extreme cases, this may require the removal of carpeting, section of walls, etc. However, the invention is intended to neutralize and remove these biological and organic contaminants without requiring resort to such extreme measures in some instances.

Next, the plurality of temperature indicating and pressure measuring probes 14 and 18 are placed in predetermined locations as indicated in block (104) to assure that the required temperature levels are achieved. In some cases the probes 14 can be read directly, although preferably they are connected by wires or wireless means to the console 16, so that all probes 14 and 18 can be monitored conveniently and the data recorded in real time.

When the enclosed structure 12 is sealed, at least one inlet duct 24 and at least one outlet duct 26 are then installed as indicated in block (106). Generally, a plurality of inlet ducts 24 is preferred. Although each duct 24 may enter the enclosed structure 12 separately, the use of one inlet duct 24 connected to a manifold from which plural ducts extend to predetermined locations within the enclosed structure 12 is preferred. Ducts 24 may enter the structure 12 through any suitable opening, such as an open window or door with the remainder of the window or door blocked by a panel.

The appropriate air scrubbing filters and vacuum devices 28 for facilitating the removal of the heated air and filtering the harmful substances therefrom, is installed, as indicated in block (108).

When the components of the system 10 have been properly prepared and positioned, a negative pressure is established within the structure 12 (110). This is accomplished using the vacuum/blower device 28 as described above. Using the pressure measuring manometer device 18, the internal pressure of the structure is measured and it is verified that sufficient negative pressure is present (112). Typically, the establishment of negative pressure is performed before any heat is introduced into the structure in order to begin the removal of any loose and aerosolized contaminants, and prevent their sporulation before heat is introduced.

Heated air (and moisture, if desired) is then directed into the inlet ducts 24 (114). Flow of the heated air through the enclosed structure 12 may range in time from a few hours to several days to provide optimum results. During this time, the temperature probes 14 are monitored (116) and these results recorded in real time (118) to ensure that the intended areas within the structure 12 are properly treated.

The heated air which has been circulated through the structure 12 is continually removed through an air scrubber filter to remove the remains of the destroyed organisms and VOCs.

At any time during system operation, the inlet and outlet ducts 24 and 26 may be moved to assure uniform temperatures throughout the structure, as indicated by the temperature probes 17 and temperature monitoring console 16.

After a predetermined period of time in which it has been determined that the harmful biological organisms and agents have been destroyed, moisture, if previously introduced is removed from the heated airstream, and after sufficient drying has taken place, the heating of air is halted and non-heated ambient air is introduced into the structure (120). The air from the structure is then exhausted through the air filter while the negative pressure is maintained for a predetermined period of time. These steps are taken in order to prevent any viable fungi, molds, etc. from sporulating or the like as such organisms when threatened with destruction will often sporulate or form cysts or the like to facilitate the survival of the organisms and their progeny. By removing the heat from the structure, any viable biological organisms will not be threatened and cease to sporulate or take other such measures. The aggressive air flow through the structure continues to remove the harmful organisms, organic substances, etc. for some time.

This entire process may often be completed in five to twelve hours, allowing a business to be closed for only one day or a residential structure to be fully treated during a typical work or school day. However, in certain circumstances, such as in the case of large structures or high levels of harmful substances within the structure, the process may be extended to several days or more to ensure that the structure is properly treated. It has been found that while harmful organisms are killed and removed during this process, the reduction of the VOCs actually continues for some time after treatment. Placing a filtering system within the structure and/or opening a window to allow the structure 12 to properly vent is believed to be adequate to remove these residual compounds.

In certain instances, the structure 12 is then physically cleaned (124) after the aforementioned steps have been performed. For example, when dealing with the hanta virus, the health concerns of the workers dictate that the virus be killed and removed to the greatest extent possible. Then, after the virus has been destroyed and removed to the greatest extent possible utilizing the aforementioned steps, workers can enter the structure and physically remove rodent droppings and the like which may contain the neutralized viruses. Samples and specimens may be taken of the previously contaminated areas to verify the desired results (126) and a physical examination of the structure can be used to verify the removal of the contagions and harmful substances.

Although an embodiment has been described in detail for purposes of illustration, various modifications may be made without departing from scope and spirit of the invention. Accordingly, the invention is not to be limited, except as by appended claims.

What is claimed is:

1. A method for destroying and removing harmful biological organisms, including molds and fungi, and chemical substances from an enclosure, comprising the steps of:

positioning at least one temperature probe at a predetermined location within the structure;

positioning a manometer within the structure to measure the pressure within the structure;

controlling the egress of air from the enclosure with respect to the ingress of air into the enclosure to create a negative pressure within the structure;

directing heated air into the structure and distributing the heated air until an interior of the structure rises to a predetermined temperature of between 110° F. and 400° F. to cause the harmful biological or chemical substances in the structure to be destroyed or migrate into the ambient air;

introducing moisture into the heated air to increase the humidity of the air;

monitoring the temperature of the structure until the predetermined temperature is achieved;

monitoring pressure levels within the structure to verify adequate negative pressure;

aggressively moving the air within the structure; and removing the heated air from the structure through a filter.

2. The method of claim 1, including the step of physically cleaning a contaminated portion of the enclosure to prepare the structure.

3. The method of claim 1, including the step of physically cleaning a contaminated portion within the enclosure after the removing step.

4. The method of claim 1, wherein the filter comprises a high efficiency particulate arrestance filter.

5. The method of claim 1, wherein the filter comprises a carbon filter.

6. The method of claim 1, including the step of protecting heat-sensitive articles within the enclosure.

7. The method of claim 6, including the step of covering the articles with an insulated mat.

8. The method of claim 6, including the step of directing the flow of heated air away from the heat sensitive articles.

9. The method of claim 1, including the step of directing non-heated ambient air into the enclosure after a predetermined time of directing heated air into the enclosure, while continuing to remove the air through the filter.

10. The method of claim 1, including the step of aerosolizing the harmful microbiological organisms or chemicals into the air within the enclosure.

11. The method of claim 1, wherein the heated air carrying the harmful substances is removed from the enclosure through a filter.

12. A method for destroying and removing harmful microbiological, including molds and fungi, and chemical substances from an enclosure, comprising the steps of:

positioning a plurality of temperature probes at predetermined locations within the structure;

positioning a manometer within the structure to measure the pressure within the structure;

controlling the egress of air from the enclosure with respect to the ingress of air into the enclosure to create a negative pressure within the structure;

directing humidified heated air into the structure and distributing the heated air until an interior of the structure rises to a predetermined temperature of between 110° F. and 400° F. to cause the harmful microbiological or chemical substances in the structure to be destroyed or migrate into the ambient air;

monitoring the temperature of the structure until the predetermined temperature is achieved;

monitoring pressure levels within the structure to verify adequate negative pressure;

aggressively moving the air within the structure to aerosolize the microbiological and organic substances;

removing the heated air carrying the harmful substances from the structure through a filter;

after a predetermined period of time, directing non-heated air into the structure; and removing the non-heated air from the structure through the filter.

13. The method of claim 12, including the step of physically cleaning a contaminated portion of the structure to prepare the structure.

14. The method of claim 12, including the step of physically cleaning a contaminated portion of the structure after the non-heated air removing step.

15. The method of claim 12, including the step of protecting heat-sensitive articles within the structure.

16. A method for removing harmful biological and organic substances from an enclosed structure, comprising the steps of:

physically cleaning a contaminated portion of the structure;

positioning a plurality of temperature probes at predetermined locations within the structure;

positioning a manometer within the structure to measure the pressure within the structure;

protecting heat-sensitive articles within the structure;

creating a negative pressure within the structure;

directing humidified heated air into the structure and distributing the heated air until an interior of the structure rises to a predetermined temperature of between 110° F. and 400° F. to cause the harmful substances in the structure to be destroyed or migrate into the ambient air;

introducing a biocide into the heated air;

monitoring the temperature of the structure until the predetermined temperature is achieved;

monitoring pressure levels within the structure to verify adequate negative pressure;

aggressively moving the air within the structure to aerosolize the biological and organic substances;

removing the heated air carrying the harmful substances from the structure through a filter;

after a predetermined period of time, directing non-heated air into the structure; and removing the non-heated air from the structure through the filter.

17. The method of claim 16, wherein the physically cleaning step comprises cleaning a contaminated portion of the structure to prepare the structure.

18. The method of claim 16, wherein the physically cleaning step comprises cleaning a contaminated portion of the structure after the non-heated air removing step.

* * * * *